United States Patent
Parmar (10) Patent No.: US 7,412,458 B2
(45) Date of Patent: Aug. 12, 2008

(54) METHOD, SYSTEMS AND APPARATUSES FOR MANAGING SPECIALIZED HEALTHCARE NEEDS

(75) Inventor: Rohit J. Parmar, Dallas, TX (US)

(73) Assignee: Cardiovascular Provider Resources, Inc., Dallas, TX (US)

( * ) Notice: Subject to any disclaimer, the term of this patent is extended or adjusted under 35 U.S.C. 154(b) by 391 days.

(21) Appl. No.: 09/934,735

(22) Filed: Aug. 22, 2001

(65) Prior Publication Data

US 2003/0041061 A1 Feb. 27, 2003

(51) Int. Cl.
*G06F 17/30* (2006.01)

(52) U.S. Cl. .................... 707/104.1; 600/508; 600/300; 600/301

(58) Field of Classification Search ............ 705/2, 705/3; 709/202; 707/10, 102, 104, 3, 9, 707/1, 104.1; 600/300, 301, 508; 434/236, 434/238; 128/923; 715/513
See application file for complete search history.

(56) References Cited

U.S. PATENT DOCUMENTS

| | | | | |
|---|---|---|---|---|
| 4,315,309 A | * | 2/1982 | Coli ................................. 705/3 |
| 4,916,441 A | * | 4/1990 | Gombrich .................... 345/169 |
| 5,052,374 A | * | 10/1991 | Alvarez-Jacinto ............ 600/218 |
| 5,301,105 A | | 4/1994 | Cummings et al. |
| 5,652,842 A | * | 7/1997 | Siegrist et al. .................. 705/2 |
| 5,772,585 A | * | 6/1998 | Lavin et al. ................... 600/300 |
| 5,840,019 A | * | 11/1998 | Wirebaugh ................... 600/300 |
| 5,926,526 A | * | 7/1999 | Rapaport et al. ......... 379/88.25 |
| 6,004,276 A | * | 12/1999 | Wright et al. ................ 600/508 |
| 6,006,191 A | * | 12/1999 | DiRienzo ........................ 705/2 |
| 6,088,429 A | * | 7/2000 | Garcia ...................... 379/88.22 |
| 6,106,301 A | * | 8/2000 | Merril ......................... 434/262 |
| 6,168,563 B1 | * | 1/2001 | Brown ......................... 600/301 |
| 6,192,112 B1 | * | 2/2001 | Rapaport et al. .......... 379/88.22 |
| 6,230,142 B1 | * | 5/2001 | Benigno et al. ................. 705/3 |
| 6,260,021 B1 | * | 7/2001 | Wong et al. ..................... 705/2 |
| 6,283,761 B1 | * | 9/2001 | Joao ........................... 434/236 |
| 6,347,329 B1 | * | 2/2002 | Evans ......................... 709/202 |
| 6,383,150 B1 | * | 5/2002 | Stewart et al. .............. 600/595 |
| 6,478,736 B1 | * | 11/2002 | Mault ......................... 600/300 |
| 6,604,115 B1 | * | 8/2003 | Gary et al. ................ 707/104.1 |
| 6,665,647 B1 | * | 12/2003 | Haudenschild ................. 705/2 |
| 6,802,810 B2 | * | 10/2004 | Ciarniello et al. ........... 600/300 |
| 6,938,206 B2 | * | 8/2005 | Ingle et al. ................... 715/530 |
| 6,963,907 B1 | * | 11/2005 | McBride et al. ............. 709/219 |
| 7,028,049 B1 | * | 4/2006 | Shelton .................... 707/104.1 |
| 7,099,801 B1 | * | 8/2006 | McBride et al. ............. 702/188 |
| 7,223,236 B2 | * | 5/2007 | Brown ......................... 600/300 |
| 7,258,666 B2 | * | 8/2007 | Brown ......................... 600/300 |
| 2002/0007284 A1 | * | 1/2002 | Schurenberg et al. .......... 705/2 |
| 2002/0046346 A1 | * | 4/2002 | Evans ......................... 713/200 |
| 2002/0128871 A1 | * | 9/2002 | Adamson et al. ............... 705/3 |
| 2002/0178031 A1 | * | 11/2002 | Sorensen et al. ............... 705/2 |
| 2003/0105648 A1 | * | 6/2003 | Schurenberg et al. .......... 705/2 |
| 2003/0105649 A1 | * | 6/2003 | Sheiner et al. ................. 705/2 |

(Continued)

*Primary Examiner*—Jean M Corrielus
(74) *Attorney, Agent, or Firm*—Gardere Wynne Sewell LLP (57) ABSTRACT

The present invention provides a healthcare management system for specialized healthcare needs. The healthcare management system may include at least one database. The healthcare management system may also include a data collection module. The data collection module is in communication with the database and may be configured to collect and store patient test data, patient information, and healthcare provider information.

20 Claims, 12 Drawing Sheets

U.S. PATENT DOCUMENTS

| | | | | |
|---|---|---|---|---|
| 2004/0084895 A1* | 5/2004 | Blum | ............................ | 283/75 |
| 2004/0128165 A1* | 7/2004 | Block et al. | ..................... | 705/2 |
| 2004/0260577 A1* | 12/2004 | Dahlin et al. | ................... | 705/2 |
| 2005/0080652 A1* | 4/2005 | Brown | ............................ | 705/2 |
| 2007/0100665 A1* | 5/2007 | Brown | ............................ | 705/3 |
| 2007/0213608 A1* | 9/2007 | Brown | ......................... | 600/316 |
| 2007/0287895 A1* | 12/2007 | Brown | ......................... | 600/301 |

* cited by examiner

Main Form

Non-Invasive L 640

HeartPlace
411 N. Washington, Suite 40
Dallas, TX 75246
(214) 841-2000

Pt.Name (Last, First): ABBOTT, KATHLEEN
HP Acct ID#: L3410
Test Date: 7/19/2000
DOB: 1/7/1967    Sex: F    Age: 33
Pt Phone: 940 464 0309    Tape #: 2268

HP MD: Kevin R. Wheelan, M.D.
HP Technician: Blundell, Angela
ConsultMD: COHN MD, PETER D    Phone: 214 750-6711    Fax: 214 750-6226
ConsultMD2:    Phone:    Fax:

2D Echo/Doppler

DOPPLER VALVE DATA:

AORTIC VALVE  — Normal Values
- Peak Velocity: 1.5 m/s (0.5-1.8 m/s)
- LVOT Velocity: m/s
- Mean Gradient: mmHg
- Maximum Gradient: 9.0 mmHg
- LVOT Diameter: cm
- AV Area: cm²
- Regurgitation: ☑ None ☐ Trace ☐ Mild ☐ Mod ☐ Severe

MITRAL VALVE
- Peak Velocity E wave: 0.8 m/s (0.4-1.3 m/s)
- Peak Velocity A wave: 0.6 m/s (0.4-1.3 m/s)
- Deceleration Time: msec
- Mean Gradient: mmHg
- Pressure Half Time: msec (20-60)
- MV area: cm²
- Regurgitation: ☐ None ☐ Trace ☑ Mild ☐ Mod ☐ Severe

TRICUSPID VALVE
- Peak Velocity: 0.9 m/s (0.3-1.0 m/s)
- TR Velocity: 2.0 m/s
- ERAP: 10 mmHg
- Est RV systolic pressure: 26.0 mmHg (4V² + ERAP)
- Regurgitation: ☐ None ☐ Trace ☑ Mild ☐ Mod ☐ Severe

PULMONIC VALVE
- Peak Velocity: 0.8 m/s (0.5-1.5 m/s)
- Acceleration Time: msec
- Regurgitation: ☐ None ☐ Trace ☑ Mild ☐ Mod ☐ Severe

MEASUREMENTS:

| | Measured Values | Normal Values |
|---|---|---|
| SEPTUM | 0.7 | CM (0.6 -1.1) |
| POST. WALL | 1.1 | CM (0.6 -1.1) |
| LVEDD | 4.4 | CM (3.5 -5.7) |
| LVESD | 2.5 | |
| AORTA | 2.6 | CM (2.0 -3.7) |
| AO VALVE | 2.1 | |
| L ATRIUM | 2.9 | CM (0.9 - 4.0) |
| RV DIAST | 2.0 | CM (0.9 - 2.6) |

Wall Motion

| | NORMAL | HYPO | AKIN | DYSKIN |
|---|---|---|---|---|
| Anterior | ☑ | ☐ | ☐ | ☐ |
| Septum | ☑ | ☐ | ☐ | ☐ |
| Inferior | ☑ | ☐ | ☐ | ☐ |
| Posterior | ☑ | ☐ | ☐ | ☐ |
| Lateral | ☑ | ☐ | ☐ | ☐ |
| Apex | ☑ | ☐ | ☐ | ☐ |

Ejection Fraction (EF) = Approx 65 to 70 %

IV Contrast: ☑ Yes
IV Contrast Reason:

Tissue Doppler: ☐ Yes ☑ No

CONCLUSIONS:
Technical Quality: ☐ Technically Difficult ☑ Good

2D ECHO/COLOR DOPPLER REVEALING NORMAL LV SYSTOLIC/DIASTOLIC FUNCTION AND CHAMBER SIZES. THERE IS MILD MR NOTED WITHOUT PROLAPSE.

HP Reading MD: Charles M. Gottlich, M.D.
Reading Dates: Original: 7/19/2000    Revised:
Not Valid without Digital Signature.

"DIGITALLY VERIFIED SIGNATURE DIGITALLY VERIFIED SIGNATURE"

View Tests by Patients
- Lists all tests done for a given patient –

Fig. 9

Print Signed Tests
--Allows users to print tests read on any day specified, for any one or group of locations.
--Users may alos list all test in the system that have not been read by a doctor

FIG. 10

METHOD, SYSTEMS AND APPARATUSES FOR MANAGING SPECIALIZED HEALTHCARE NEEDS

TECHNICAL FIELD OF THE INVENTION

The present invention relates generally to the field of healthcare management and more particularly to methods, systems and apparatuses for managing specialized healthcare needs.

BACKGROUND OF THE INVENTION

Without limiting the scope of the invention, its background is described in connection with healthcare management systems. The management of information is important in many aspects of many businesses. In the healthcare industry, the management of information and data becomes even more important. Typically, data is maintained in paper form by healthcare providers. Once a patient has a test conducted, a paper report is generated with the results of the test. These reports are then stored in different locations under different systems for maintaining their integrity.

The storage of paper information poses dilemmas for specialized healthcare needs, such as cardiological care. Patients with cardiological problems often have multiple tests performed during doctor's visits or experience more frequent tests than other patients. These tests can examine different aspects of their condition and allow doctors to determine different methods of treatment. Many times, however, these tests must be conducted at different locations or by different doctors. Because a paper system is more difficult to relay from provider to provider, the files are usually maintained by the provider who performs the tests. Thus, when a doctor needs to examine multiple tests at the same time, the doctor must contact the various service providers or locations in order to retrieve the test results. This presents difficulty in performing a comprehensive diagnosis, and can lead to inefficiencies and delays in clinical analyses.

SUMMARY OF THE INVENTION

The present invention provides a healthcare management system for specialized healthcare needs. The healthcare management system may include at least one database. The healthcare management system may also include a data collection module. The data collection module is in communication with the database and may be configured to collect and store patient test data, patient information, and healthcare provider information.

A data viewing module may also be provided by the healthcare management system. The data viewing module is in communication with the database and may be configured to allow access to and modification of the patient test data. The healthcare management system may further provide a patient access module. The patient access module may be in communication with the database and may be configured to allow access by a user to view tests performed on a patient. The healthcare management system may also provide a form generation module. The form generation module may be in communication with the database and may be configured to produce reports from the patient test data.

The present invention also provides a method of managing specialized healthcare needs. The method may include the steps of collecting patient test data using one or more test forms, organizing the patient test data according the patient and test performed, editing the patient test data, securing the patient test data, and generating a report for the tests performed from the patient test data.

The present invention further provides a computer program embodied on a computer readable medium for managing specialized healthcare needs. The computer program includes a code segment to create one or more test forms. The computer program also includes a code segment to collect patient test data using the one or more test forms. In addition, the computer program may include a code segment to organize the patient test data according to patient and test performed. The computer program may further provide a code segment to edit the patient test data. The computer program may also provide a code segment to secure the patient test data. Additionally, the computer program may provide a code segment to generate a report of the test performed from the patient test data.

BRIEF DESCRIPTION OF THE DRAWINGS

For a more complete understanding of the features and advantages of the present invention, reference is now made to the detailed description of the invention along with the accompanying figures in which the corresponding numerals and the different figures refer to corresponding parts and in which:

FIG. 6a is a screen shot showing a test data entry form of the present invention;

DETAILED DESCRIPTION OF THE INVENTION

While the making and using of various embodiments of the present invention are discussed in detailed below, it should be appreciated that the present invention provides many applicable inventive concepts that may be embodied in a wide variety of specific context. The specific embodiments discussed herein are merely illustrative of specific ways to make and use the invention and do not limit the scope of the invention.

The present invention provides a software application that can operate on a wide variety of hardware configurations. These configurations range from a single machine, single database installations to large installations with multiple machines and databases. As a result, the present invention can be easily scaled up to meet added demand by increasing the number of machines and databases within the system to match the increase in number of users.

Figure 1:
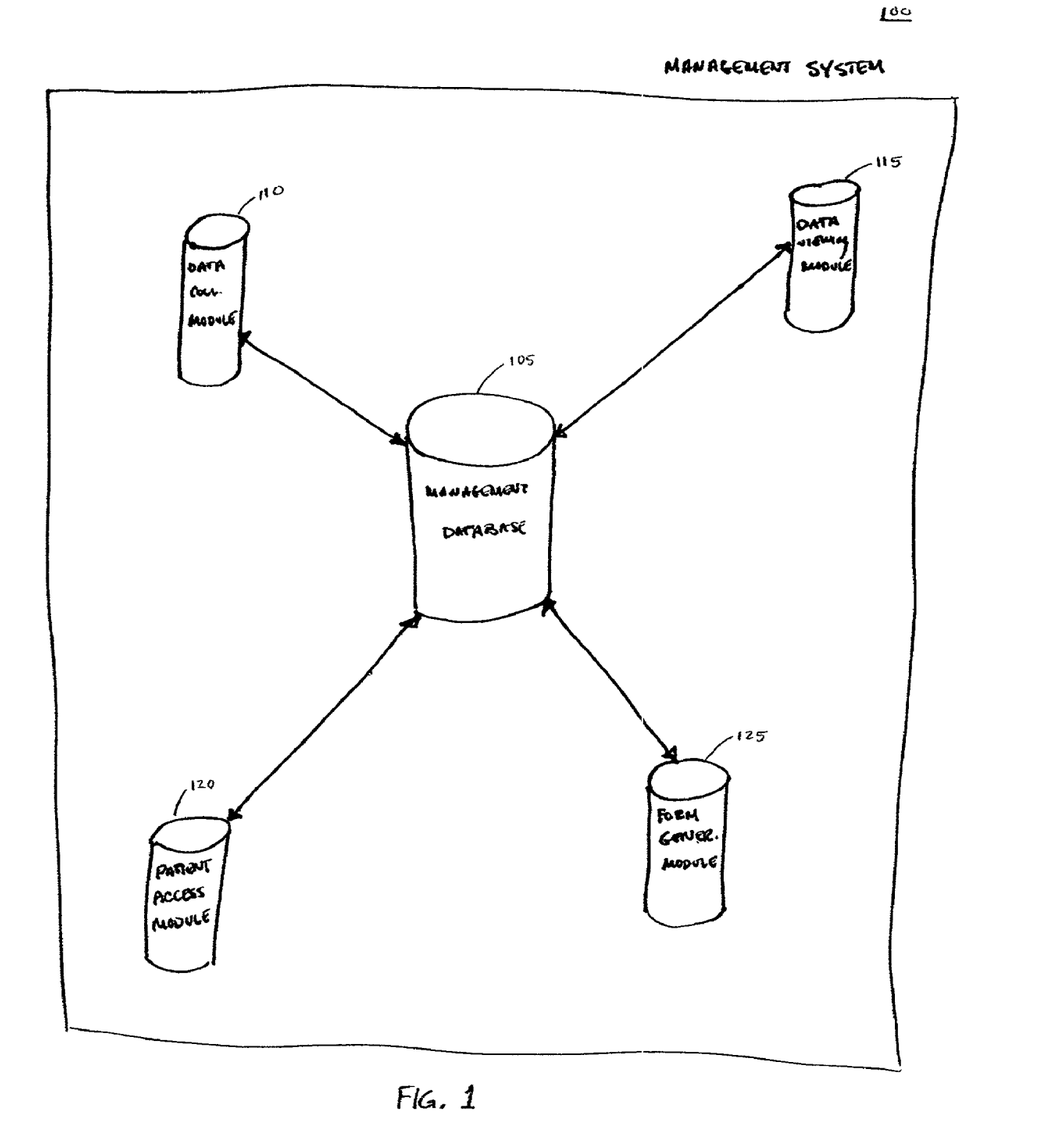
FIG. 1 is a schematic diagram of the management system of the present invention.

The present invention is depicted in FIG. 1 generally as 100. The healthcare management application 100 comprises several modules and at least one database. As depicted, at least one management database 105 can be used as central storage facility for all data collected using the healthcare management application 100. A data collection module 110 may be in communication with the management database 105. The data collection module 110 may be configured to allow the creation of test data entry forms for test data collection. The data collection module 110 may include a variety of test data entry forms created for the healthcare management application 100. The data collection module 110 may also include a patient information form to collect information regarding a particular patient. The patient information may also be collected using the test data entry forms. In addition, the data collection module 110 may include a physician/technician information form. The physician/technician information may also be collected using the test data entry forms.

The data collection module 110 allows the user to select a test for which data for a particular patient will be entered. Additionally, the healthcare management system 100 includes a data viewing module 115. The data viewing module 115 may be in communication with the management database 105. The data viewing module 115 allows the user to read and edit test data entry forms that have been entered through the data collection module 110. The ability to either edit or read a test data entry form is determined by whether or not the test data entry form has been secured. As will be demonstrated in FIG. 6a, a test data entry form becomes secured if a physician affixes his electronic signature to the form.

A view test by patient module 120 can also be included in the management system 100. The view test by patient module 120 can be in communication with the management database 105. The view test by patient module 120 allows a user to view all tests performed on a particular patient. Additionally, a report generation module 125 can be included in the management system 100. The report generation module 125 can be in communication with the management database 105. The report generation module 125 allows the user to create reports of the test data that is secured on a particular day or group of days.

Figure 2:
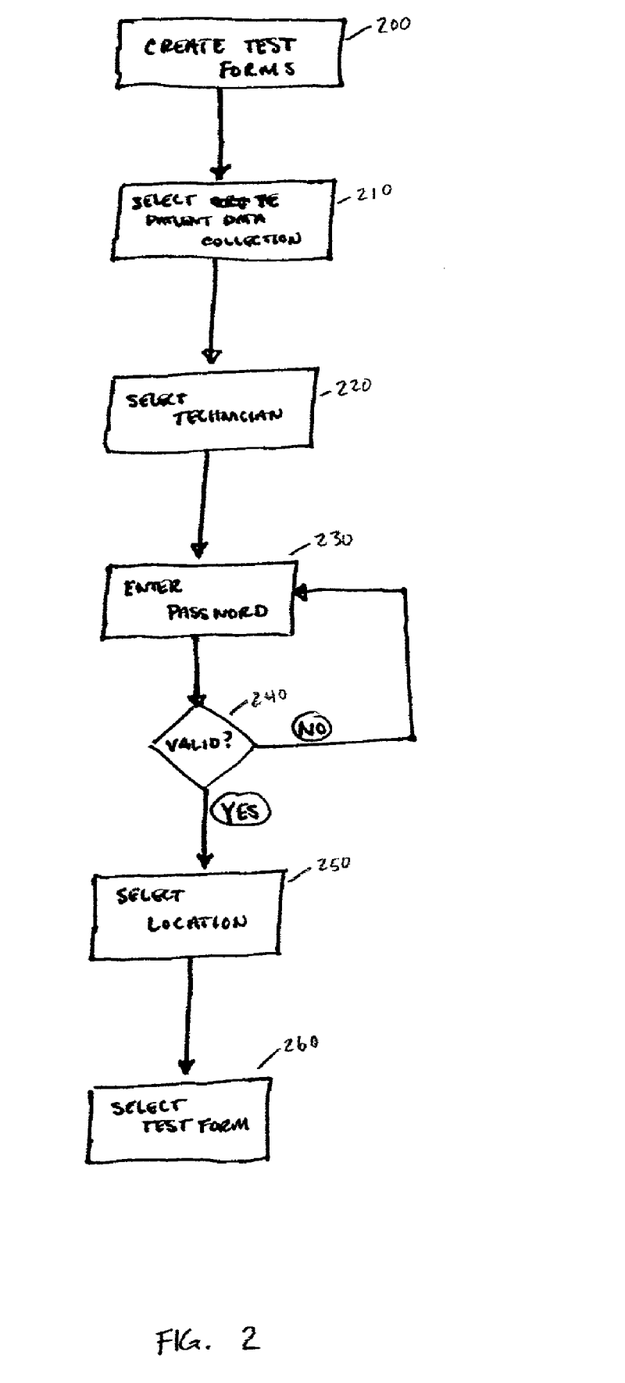
FIG. 2 is a block diagram of showing the operation of the data collection module of the present invention.

Referring now to FIG. 2, a block diagram illustrating the operation of the data collection module 110 of FIG. 1 is shown. As shown in block 200, test data entry forms are first created for the healthcare management system 100 of FIG. 1. Once these test forms have been created, a user can request to collect patient data using the healthcare management system, as in block 210. After the user requests to collect patient data, the system prompts the user to select a technician name, as in block 220. Once the technician's name has been selected, the system prompts the user to enter the password associated with the technician, as in block 230. After the user has entered the password for the technician, the system attempts to validate the password as in block 240. If the system cannot validate the password, then the system asks the user to re-enter the password. If, however, the password entered by the user is valid then the system asks the user to select a location of the facility where the test has been performed, as shown by block 250. Once the location of the testing facility has been selected, a test data entry form associated with the test performed may be selected, as depicted by block 260. After the appropriate test data entry form has been selected, the user can then enter the collected test data.

Figure 3:
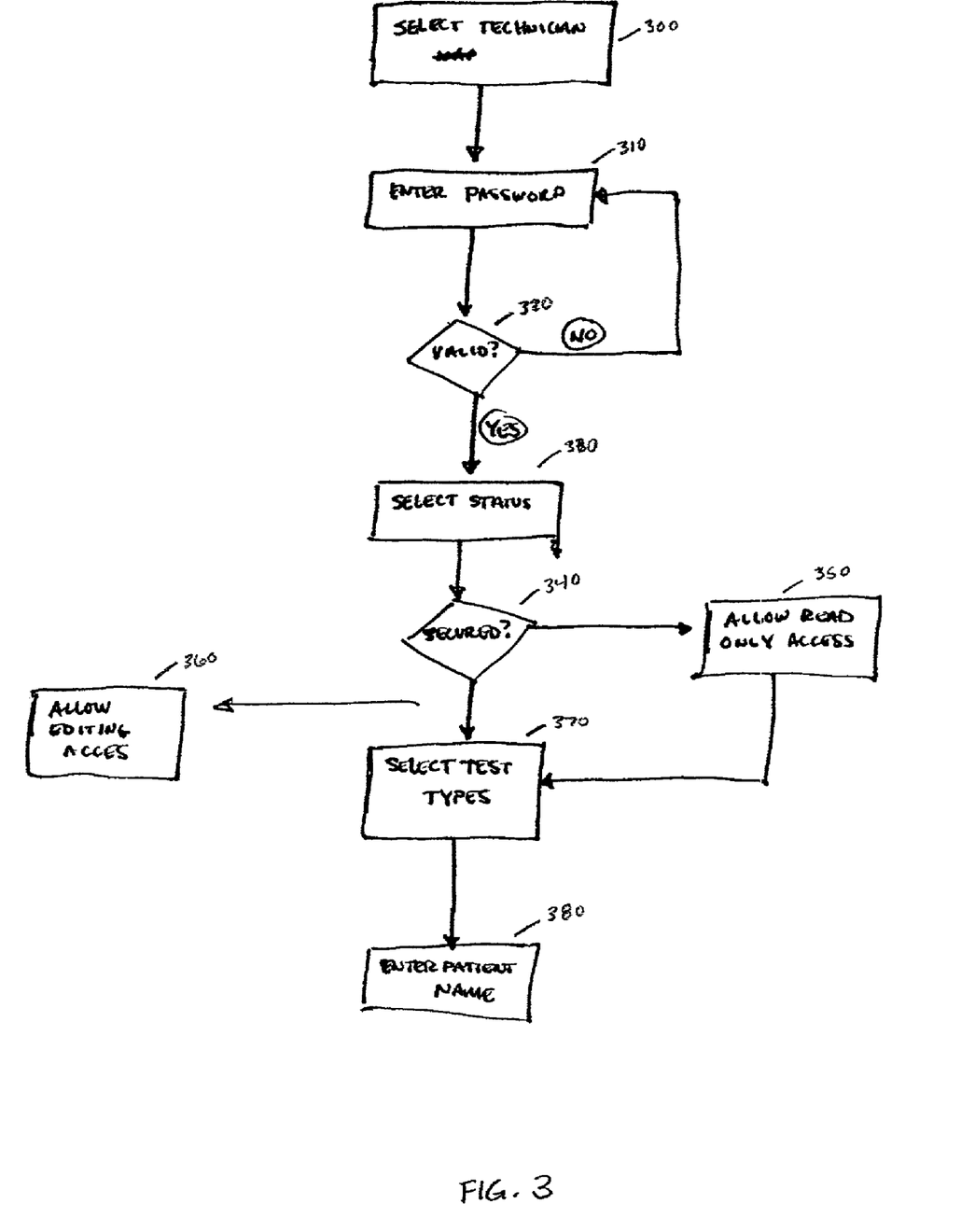
FIG. 3 is a block diagram showing the operation of the data viewing module of the present invention.

Referring now to FIG. 3, the operation of the data viewing module 115 is shown. Once the user has selected the data viewing module, the user is prompted to select a technician, as depicted in block 300. After the user has selected a technician, the user is prompted to enter a password for the technician, as shown by block 310. The data viewing module then attempts to validate the password entered by the user, as in block 320. If the password is not valid, the data viewing module prompts the user to enter a new password. If, however, the password is valid, the data viewing module asks the user to select the status of the test data entry form the user desires to view, as depicted by block 330. Several different statuses can be selected by the user. For example, the user may select "test not yet read/signed" or "test previously read/signed." Once the status of the test data entry form is selected, the system determines if the user has requested secured test data entry forms, as in block 340. If the user has selected secured test data entry forms, then the system will only allow the user to have "read-only" access to the test data entry forms, as depicted by block 350. If, however, the test data entry forms are not secured, then the data viewing module will allow the user editing access to the test data entry forms, as shown by block 360. Once "read-only" or editing access has been determined, the data viewing module then asks the user to select the types of test data entry forms to be viewed, as shown by block 370. Then, as in block 380, the user may be asked to enter the name of the patient for which the tests selected are to be shown. Once the name of the patient is entered, the test data entry form can be displayed.

Figure 4:
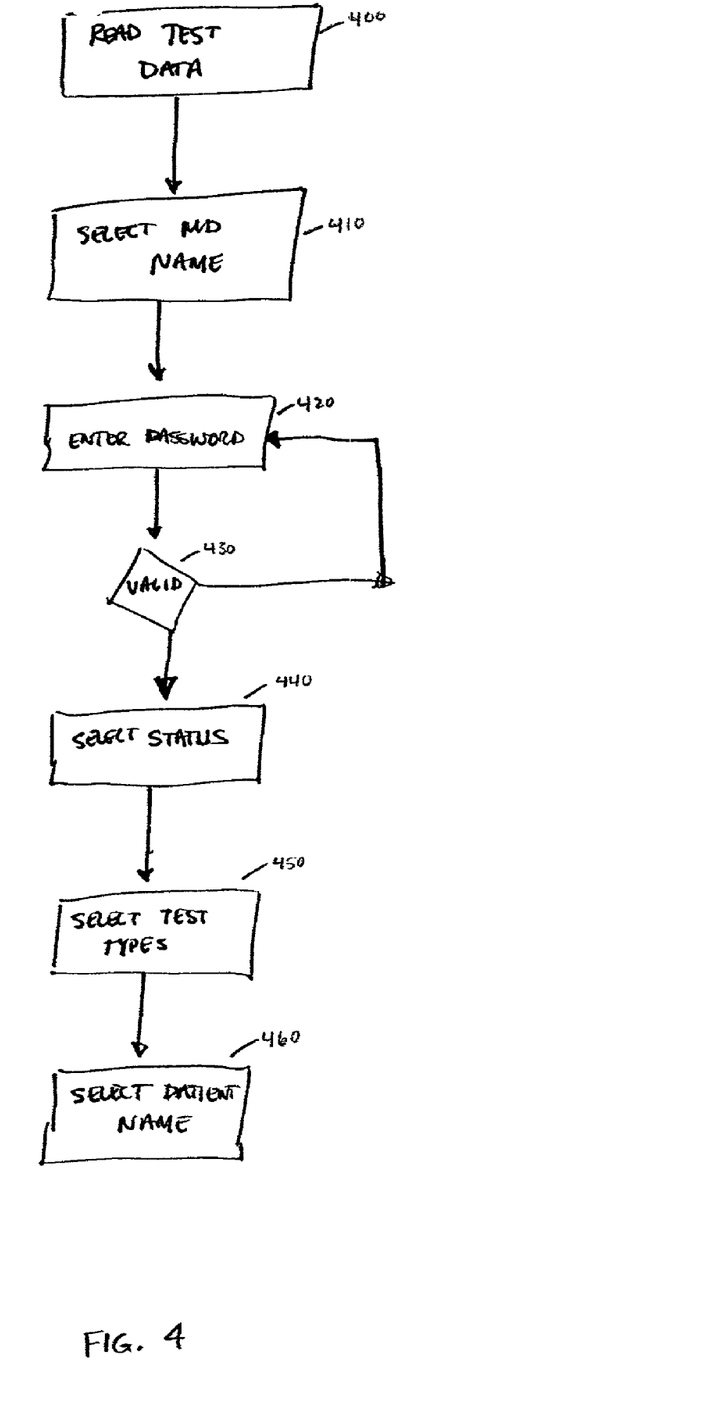
FIG. 4 is a block diagram showing the operation of the physician viewing module of the present invention.

Referring now to FIG. 4, a separate reading module for reading test data entry forms by a physician is shown through the block diagram in FIG. 4. Once the user selects to read the patient test data entry form as a physician, as in block 400, the user may be prompted to select the name of the physician, as in 410. After the name of the physician is selected, the user may prompted to enter a password for the physician as shown by block 420. Once the password is entered, the system attempts to validate the password, as in block 430. If the password is not valid, the system prompts the user to enter a new password. If, however, the password is valid, then the system requests the user to select the status of the test data entry form desired to be read, as in block 440. After the status of the test data entry form has been selected, the system prompts the user to select the test data entry form to be viewed, as in block 450. Once the test data entry form has been selected, the system prompts the user to enter the name of the patient for whom the test data entry form is to be read, as in block 460. The test data entry form may then be displayed for the user.

Referring now to FIGS. 5-10, an illustrative example of the management application and system of the present invention is generally shown. While the system shown is for cardiological care, it will be appreciated that the system may be utilized for other specialized healthcare needs such as neurological testing and the like.

Figure 5:
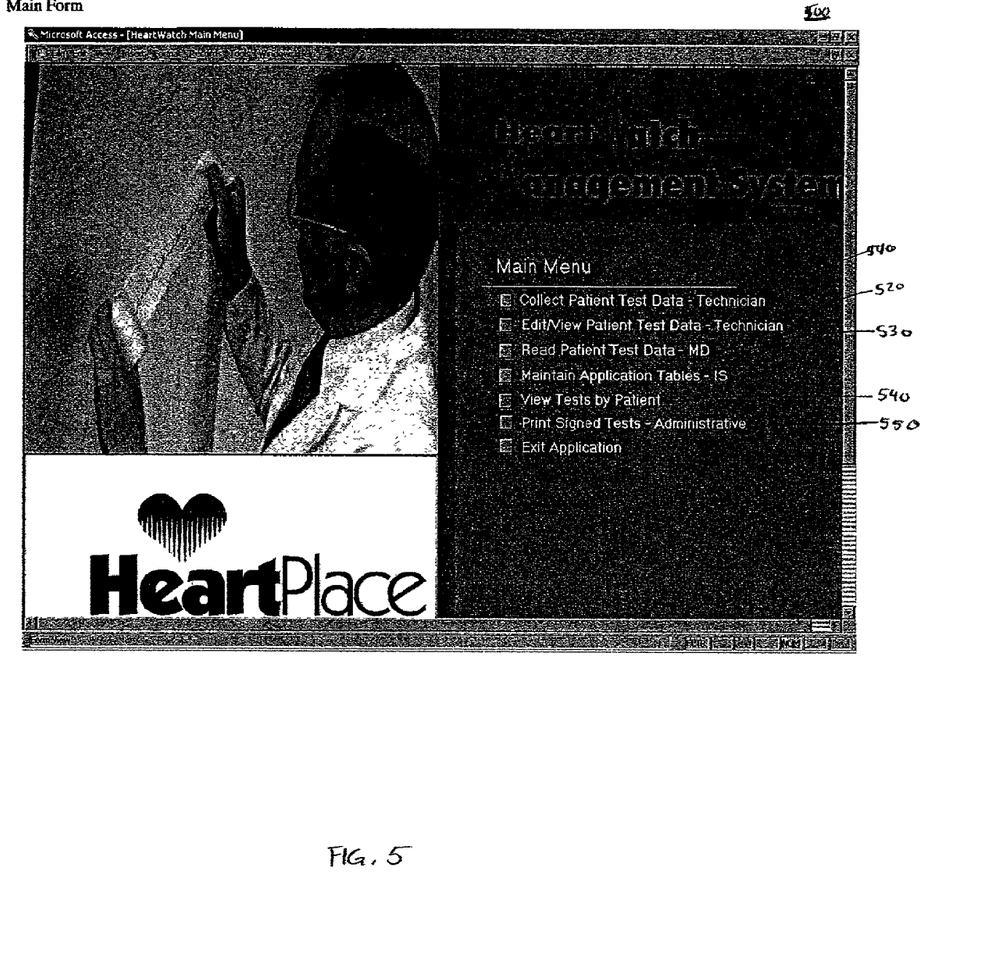
FIG. 5 is a screen shot showing the main menu screen of the present invention.

Referring now to FIG. 5, the healthcare management application is generally depicted as 500. As is shown, the menu on the screen shot in FIG. 5 shows the various modules that can be accessed by the user of the healthcare application. Referring to the menu, the data collection module is generally referred to as 510. The data viewing module is depicted as 520, the view test by patient module is depicted as 540, and the report generation module is depicted as 550. A doctor read patient module is also depicted as 530.

Figure 6:
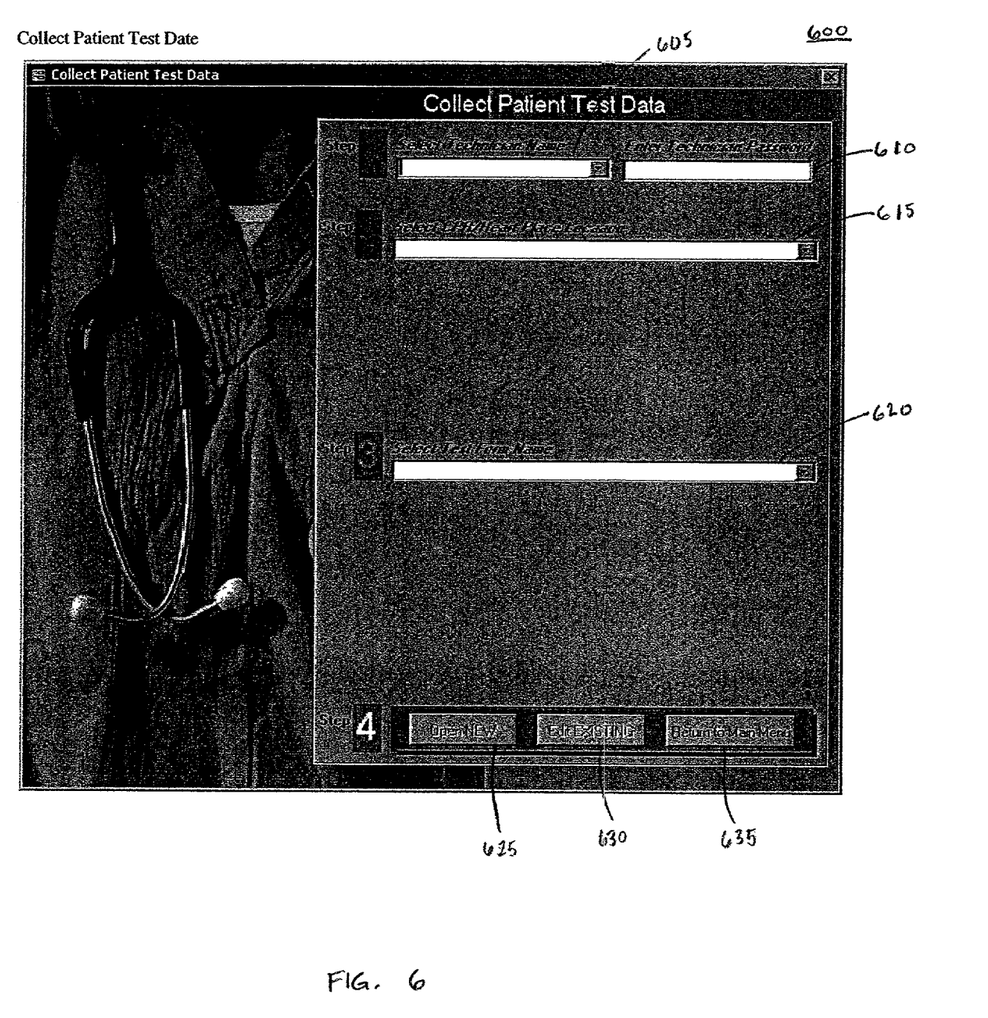
FIG. 6 is a screen shot showing the data collection module of the present invention.

Referring now to FIG. 6, the data collection module is generally depicted as 600. The data collection module allows the user to either select the name of a technician from a predetermined list or manually enter the name of the technician in slot 605. Once the name of the technician is entered, the user must enter the password of the technician in slot 610. After the password of the technician has been verified by the system, the system allows the user to select a location where the test occurred in slot 615. Once a location has been selected, the user can then select the test data entry form for which the user would like to collect data, in slot 620. Once slot 605, 610, 615 and 620 have been completed, the user can then open a new test data entry form by selecting the open new button 625. The user can edit an existing form by selecting the edit existing button 630, or the user could return to the main menu by selecting the return to the main menu button 635.

Once the user selects either the open new button 625, a test data entry form will appear on the users screen. The test data entry form allows the user to enter various information for the test that has been conducted. If the user selects the edit existing button 630, form 700 (depicted in FIG. 7) opens for the user to fill out.

Figure 6B:
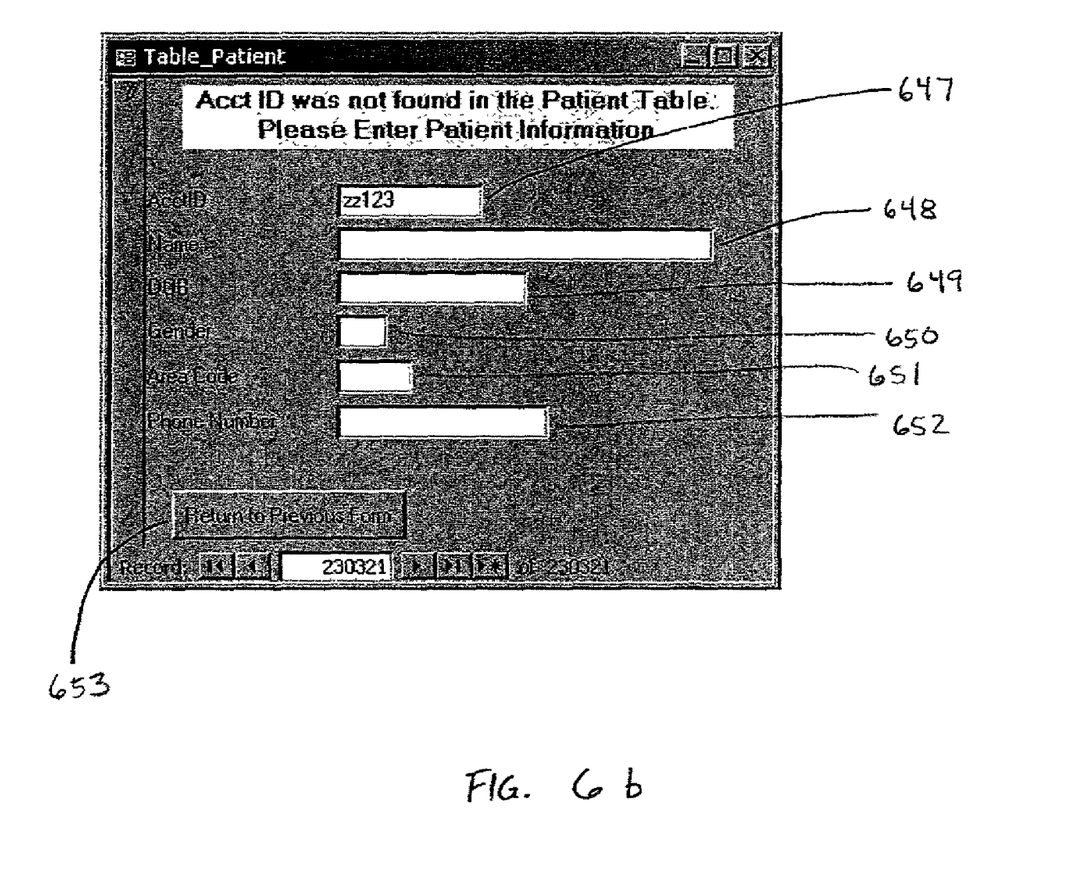
FIG. 6b is a screen shot showing a patient information form of the present invention.

Referring to FIG. 6a, a sample test data entry form is shown. The test data entry form in this example is for a 2D Echo/Doppler test. As is shown, the user can enter the account identification of the patient in slot 640. The test date in slot 645 defaults to the current date, or may be changed by the user to a different date. Once the account identification has been entered, the information in slot 650 is calculated, based on previously entered patient information. If the patient does not already exist in the system, a patient information form is displayed for the user, as shown in FIG. 6b. Various patient information can be entered into the patient information form. For example, the account identification for the new patient can be displayed in slot 647. The name of the patient can be entered in slot of 648. The date of birth of the patient can be entered in slot 649, the gender of the patient can be entered in slot 650, and the area code and the phone number of the patient can be in slots 651 and 652 respectively. Once the information is entered into the patient information form, the user can then return to the previous form by selecting the return to previous form button 653.

Referring back to FIG. 6a, the name of the physician can be entered in slot 655 and the name of the physician/technician entering the data can be entered in line 660. If consultant doctors are required, their names can be entered in line 655.

Once all the vital information of the patient and the doctors has been entered, the user can then turn to entering the test data in the test data portion of the screen 670. The test data portion will change depending upon which test is being conducted. Each test will have its own values and variables that will need to be entered for the test data entry form to be completed.

Figure 7:
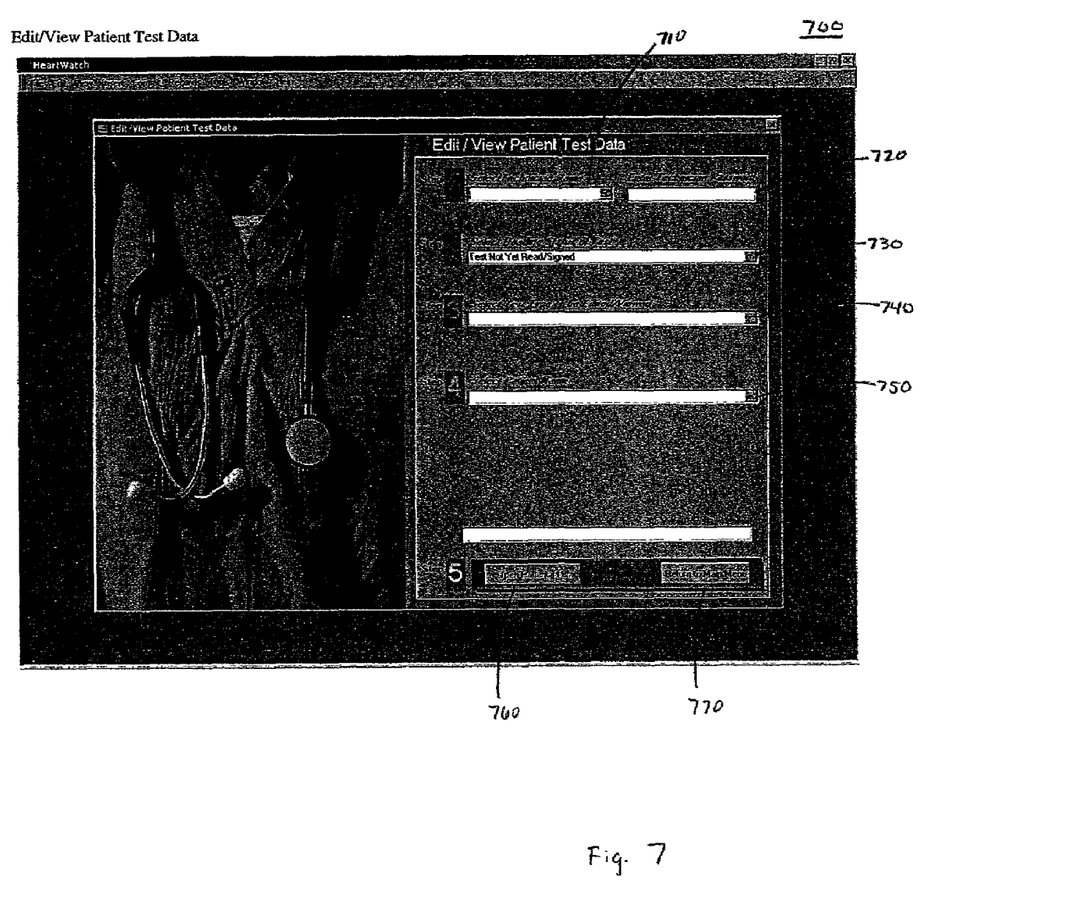
FIG. 7 is a screen shot showing the data viewing module of the present invention.

Referring now to FIG. 7, the data viewing module of the present invention is shown generally as 700. Once the user has selected the data viewing module 700, the user may enter the name of the technician desiring to edit or view a test data entry form in slot 710. After the name of the technician has been entered, the user can then enter the password of the technician in slot 720. Once the password of the technician has been verified, the user may then select the status of the test data entry form to be read in slot 730. The status of the test data entry form can vary, and may be, for example, that the test data entry form has not been read or signed, or the test data entry form has been signed. Once the status of the test data entry form has been selected, the user can then select the test data entry form to be viewed or edited from slot 740. After the test data entry form has been entered, the name of the patient for whom the user desires to view the test data entry form can be entered in slot 750. Once the user has completed slots 710 through 750, the user can then either open the test data entry form selecting the open patient button 760, or return to the main menu by selecting the return to the main menu button 770. If the user selects to open the test, the user will receive a form similar to that in 6b, but with the information completed.

Figure 8:
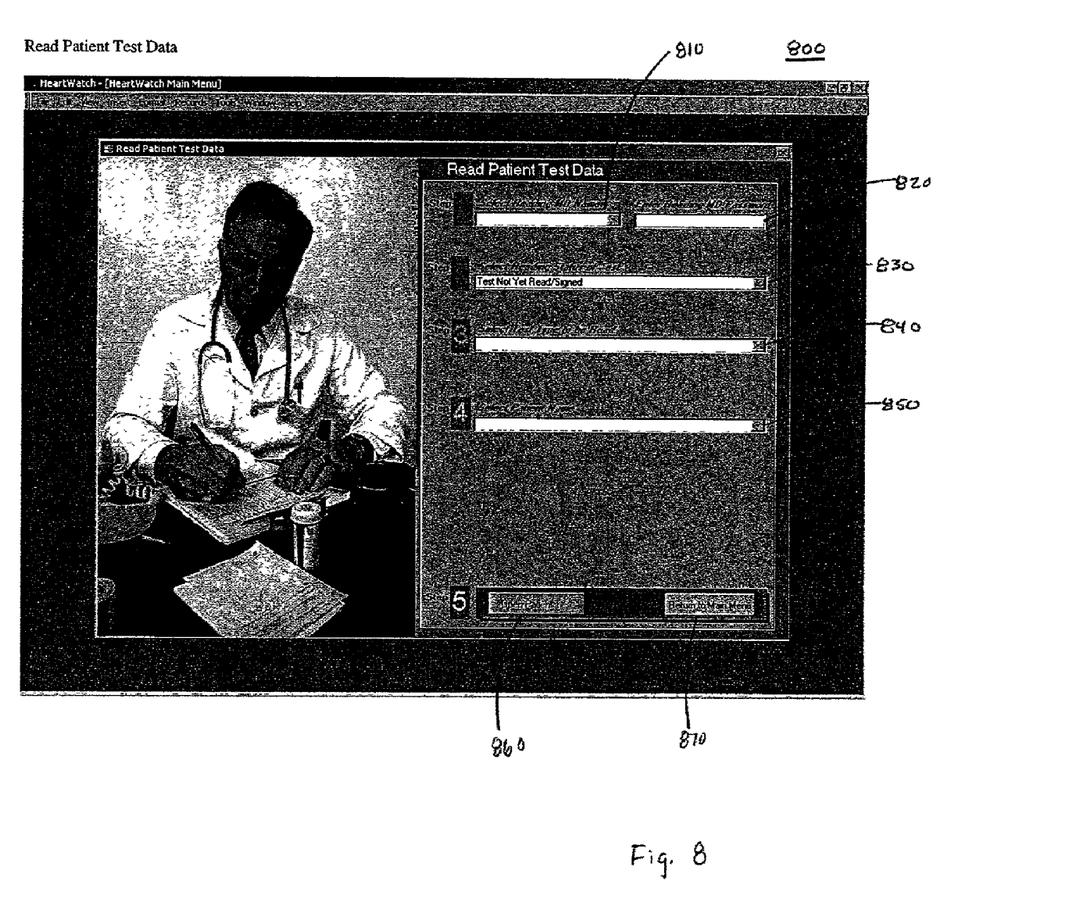
FIG. 8 is a screen shot showing the physician viewing module of the present invention.

Referring now to FIG. 8, the MD read patient test data module is generally depicted as 800. When this module is selected, the user must enter the name of the reading physician in slot 810. After entering the name of the reading physician, the user enters the password of the reading physician in slot 820. Once the system has verified that the password matches the reading physician, the system allows the user to select the status of the test in slot 830. The status of the test entry data form in this module is the same as that of FIG. 7. After the status of the test data entry form has been selected, the user can then select the test data entry form to be read in slot 840. After selecting the test data entry form, the user will then enter the name of the patient for whom the test data entry form is to be viewed, in slot 850. Once slots 810 through 850 have been completed, the user then can open the test data entry form by selecting the open patient test button 860, or return to the main menu by using the return to the main menu button 870. Again, once the user has selected the open patient test button 860, a test similar to that of FIG. 6b will appear on the screen of the user.

Referring back to FIG. 6b, after the test data has been entered as described above with reference to FIG. 8, the reading physician can enter his name in slot 675. Reading dates are automatically populated, but can also be entered in slot 680 and 685. The original reading date by a physician is entered in slot 680. If any physicians have revised the report since the original date, the revision date is populated or entered in slot 685. Once the report has been read and approved, the reading physician can affix his signature digitally to the report in slot 690. By digitally affixing the signature, the reading physician secures the document so that it may not be edited by anyone other than himself. In essence, this secures the document to "read-only" status.

Figure 9:
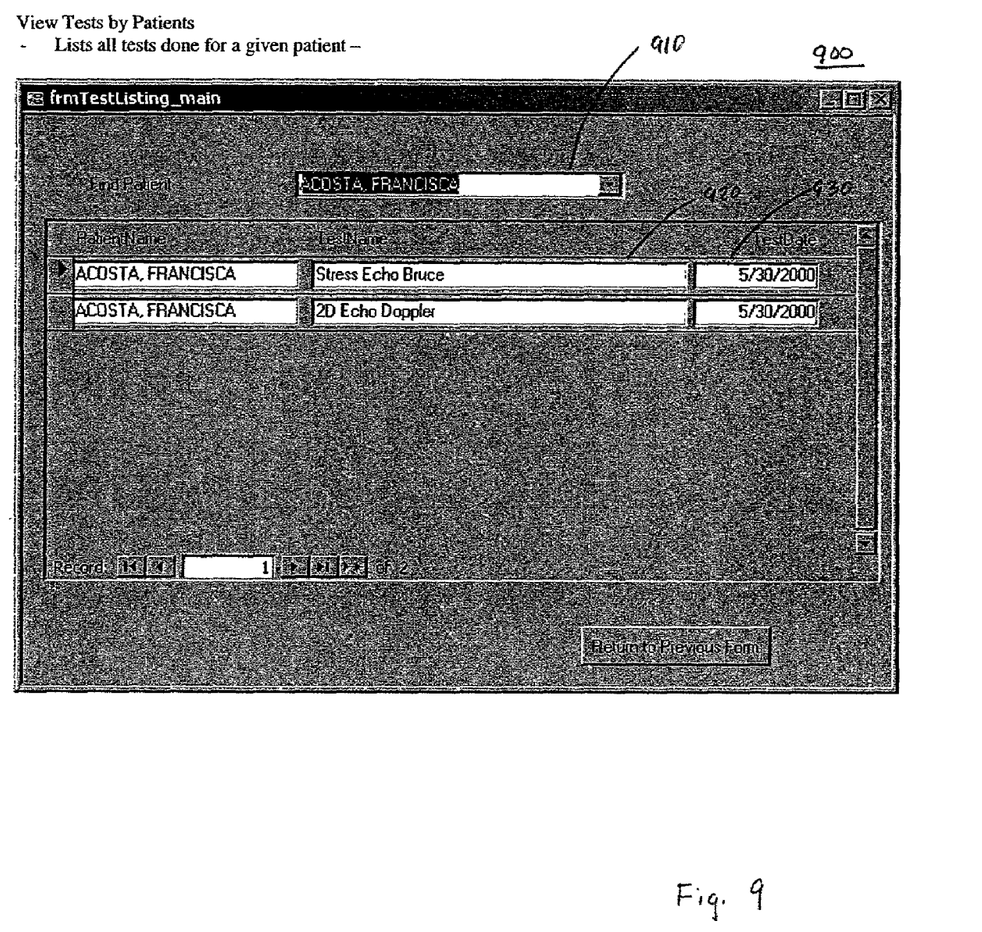
FIG. 9 is a screen shot showing the view test by patient module of the present invention.

Referring now to FIG. 9, the view test by patients module is generally depicted as 900. In this module, a user may find all the tests that have been conducted for a particular patient. The user enters the name of the patient in slot 910. Once the name of the patient has been entered, the system locates all the tests that have been performed on that patient. The tests are then listed by test name in slot 920 and test date in slot 930.

Figure 10:
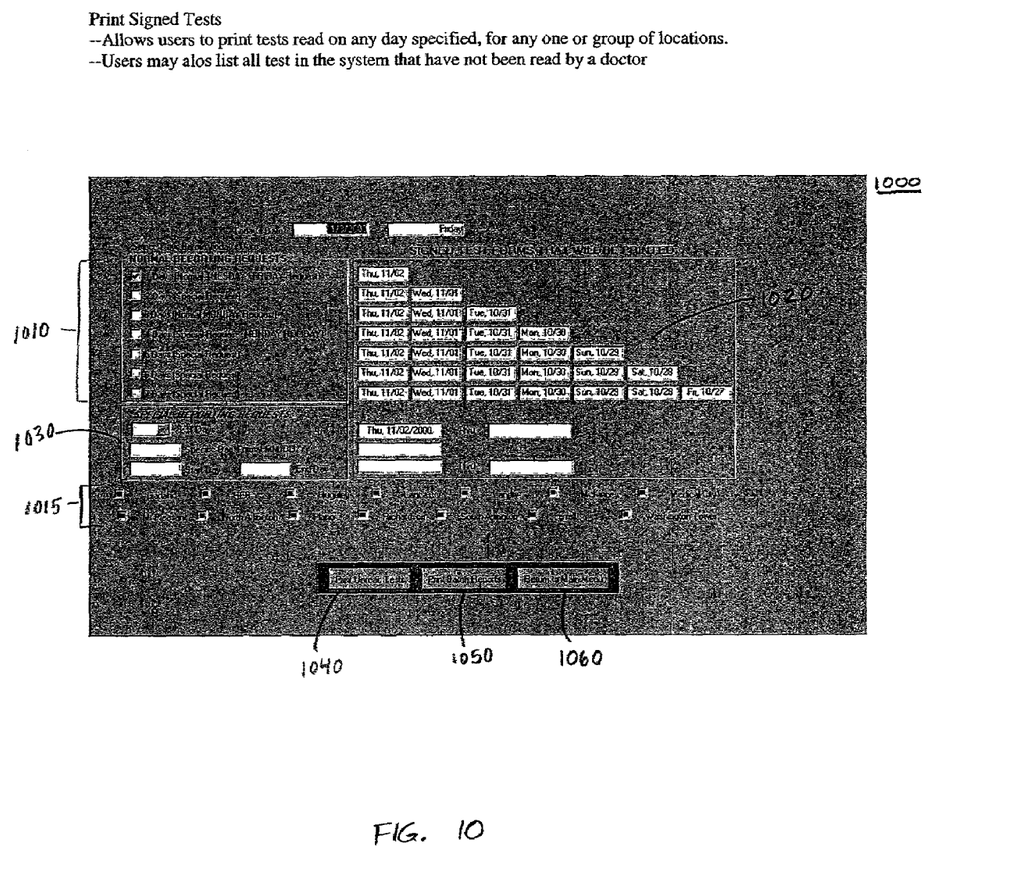
FIG. 10 is a screen shot of the report generation module of the present invention.

Referring now to FIG. 10, the report generation module is generally depicted as 1000. In the report generation module, the user can select to print test reports for doctors. The user selects how many days before today's date they would like to see tests by checking one of the day slots in 1010. The user also selects the location where the tests were performed, by selecting the location depicted as 1015. Once the day and location have been selected, tests will appear for each of the days and locations that have been selected, as shown by slot 1020. The user may also have special reporting requests, as in slot 1030. These requests may be to lengthen the amount of time for which reports will be generated, specify a day, month and year for a test, specify a start and end day for tests. Once the user has selected the days of tests that are to be printed, the user can then generate reports in two different ways. The user may print only unread test by using the print unread tests button 1040. The user may also print batch reports of several tests by using the print batch reports button 1050. Finally, the user may return to the main menu by using the return to the main menu button 1060.

What is claimed is:

1. A cardiological healthcare management system for specialized healthcare needs operable on one of a computer including a visual display and a network of computers including visual displays, respectively, comprising:
   a system management database; and
   a computer readable medium having stored therein: a data collection module in communication with the system management database and being configured to collect and store patient test data, patient information, and healthcare provider information, wherein the data collection module comprises at least one test data entry form for recording patient cardiological test data;
   a data viewing and editing module in communication with the system management database and being configured to limit access to modify the patient test data to preauthorized healthcare worker persons;
   a patient information access module in communication with the system management database and being configured to limit access to view tests performed on the patient to the preauthorized healthcare worker persons;
   a physician viewing module in communication with the system management database operable to allow preauthorized physicians to view patient test data;
   a report generation module in communication with the system management database for producing reports from one or more selected items of patient test data; and
   means for displaying an image on said visual display, said image including a listing of said modules, respectively.

2. The system set forth in claim 1 wherein:
   the data collection module includes means providing a patient test data collection image on said visual display including information entry slots requiring entry of the name and a preauthorized password of a healthcare worker person to gain access to the data collection module.

3. The system set forth in claim 2 wherein:
   the data collection module includes an information entry slot on said patient test data collection image for selecting a test data entry form for which data is to be collected.

4. The system set forth in claim 2 wherein:
   the data collection module includes means for recording account identification information of a patient whose data is to be collected and stored in the data collection module.

5. The system set forth in claim 2 wherein:
   the data collection module includes means for recording the name of a physician and the name of a person entering data in the data collection module.

6. The system set forth in claim 1 wherein:
   the data viewing and editing module includes means providing an edit and view patent test data image on said visual display and including information entry slots requiring entry of the name of the healthcare worker person and an identifier for the healthcare worker person to gain access to patient test data.

7. The system set forth in claim 6 wherein:
   the data viewing and editing module includes means permitting authorized healthcare worker persons to select a test data entry form to be viewed or edited.

8. The system set forth in claim 6 wherein:
   the data viewing and editing module includes means providing for entering the name of the patient for whom the preauthorized healthcare worker person desires to view a test data entry form.

9. The system set forth in claim 1 wherein:
   the physician viewing module includes means providing an image on said visual display for reading patient test data and including information entry slots requiring entry of the name and an identifier of a preauthorized physician desiring to read selected patient test data.

10. The system set forth in claim 9 wherein:
    the physician viewing module includes means requiring entry of the name of the patient for whom patient test data is to be read and means for selecting particular test data.

11. The system set forth in claim 1 wherein:
    the patient information access module includes means for providing information to the healthcare worker person using the system of tests that have been performed on a patient whose name has been entered in the system by way of the patient information access module.

12. The system set forth in claim 1 wherein:
    the report generation module includes means providing for preauthorized healthcare worker persons to select a date and location of specific tests that have been performed on a patient for printing by way of the report generation module.

13. The system set forth in claim 12 wherein:
    the report generation module includes means for selecting only tests which have not been previously read by a person having access to the system.

14. The system set forth in claim 1 wherein:
    the report generation module includes means providing printing of reports of plural tests performed on a patient whose name has been entered in the system.

15. A method for collecting and reporting patient test data using a cardiological healthcare management system for specialized healthcare needs operable on one of a computer including a visual display and a network of computers including visual displays, respectively, said system comprising: a processor;
    a memory coupled to the processor, and comprising:
    a system management database;
    a data collection module in communication with the system management database and being configured to collect and store patient test data, patient information, and healthcare provider information, the data collection module comprising at least one test data entry form for recording patient cardiological test data;
    a data viewing and editing module in communication with the system management database and being configured to limit access to modify the patient test data to preauthorized healthcare worker persons;
    a patient information access module in communication with the system management database and being configured to limit access to view tests performed on the patient to the preauthorized healthcare worker persons;
    a physician viewing module in communication with the system management database operable to allow preauthorized physicians to view patient test data;
    a report generation; and
    means for displaying an image on said visual display, said image including a listing of said modules, respectively, wherein said method including the steps of:
    producing reports for one or more selected items of patient test data pursuant to:
    providing an access image on said visual display;
    entering a name and a preauthorized password of a healthcare worker person in respective information entry slots of said access image to gain access to the data collection module;

selecting a test data entry form for which data is to be collected;

recording account identification information of a patient whose data is to be collected and stored in the data collection module; and recording the name of a physician and the name of a person entering data in the data collection module.

16. The method set forth in claim 15 including the steps of:

entering in the system the name of the patient for whom patient test data is to be read; and selecting particular test data.

17. The method set forth in claim 15 including the step of:

providing information to the healthcare worker person of tests that have been performed on a patient whose name has been entered in the system by way of the patient information access module.

18. The method set forth in claim 15 including the step of:

selecting a date and location of specific tests that have been performed on a patient for printing by way of the report generation module.

19. The method set forth in claim 15 including the step of:

selecting only tests which have not been previously read by a person having access to the system.

20. The method set forth in claim 15 including the step of:

printing reports of plural tests performed on a patient whose name has been entered in the system.

* * * * *